United States Patent [19]
Camprasse et al.

[11] Patent Number: 5,773,034
[45] Date of Patent: Jun. 30, 1998

[54] CUTANEOUS REJUVENATING AND HEALING PRODUCT, METHOD FOR ITS MANUFACTURE AND USES THEREOF

[75] Inventors: Georges Camprasse, Villenauxe la Petite; Serge Camprasse, Chelles, both of France

[73] Assignee: Fortune Base Management, Ltd., Central Hong Kong, Hong Kong

[21] Appl. No.: 887,605

[22] Filed: Jul. 3, 1997

Related U.S. Application Data

[63] Continuation of Ser. No. 581,526, filed as PCT/FR95/00606, May 9, 1995, published as WO95/30426, Nov. 16, 1995, abandoned.

[30] Foreign Application Priority Data

May 9, 1994 [FR] France .................................. 94 05664

[51] Int. Cl.⁶ .................................................. A61K 35/56
[52] U.S. Cl. ............................................................. 424/547
[58] Field of Search ................................................ 424/547

[56] References Cited

U.S. PATENT DOCUMENTS 4,393,045 7/1983 Henderson et al. ....................... 424/95
4,427,654 1/1984 Austin ....................................... 424/95

FOREIGN PATENT DOCUMENTS

| 1332198 | 12/1963 | France . |
| 3437184 | 4/1986 | Germany . |
| 03236319 | 10/1991 | Japan . |
| 9215276 | 9/1992 | WIPO . |

*Primary Examiner*—Jean C. Witz
*Attorney, Agent, or Firm*—Larson & Taylor

[57] ABSTRACT

Cutaneous rejuvenating and healing product comprising ground material made up of the mother of pearl testa of a bivalved mollusc and the cell dilacerate of the mollusc mantle. After being enzymatically and thermally treated, both phases are blended to a gel or cream, before being combined with excipients such as menthol, camphor, benzoin, citric acid, methyl oxibenzoate, cetylic alcohol, stearylic alcohol, officinal vaseline, glycerine, purified water, algae extract, calcium hydroxide and copra extract. The product of the invention is for dermatological and cosmetic use.

16 Claims, No Drawings

CUTANEOUS REJUVENATING AND HEALING PRODUCT, METHOD FOR ITS MANUFACTURE AND USES THEREOF

This application is a continuation of application Ser. No. 08/581,526, filed as PCT/FR95/00606, May 9, 1995, published as WO95/30426, Nov. 16, 1995, now abandoned.

BACKGROUND OF THE INVENTION

1. Field of the Invention

The present invention concerns a product manufactured from the mineral and/or organic phases emanating from *Pinctada maxima, Margaritifera* or any other aquatic bivalved mollusc, gastropod or cephalopod. The product accelerates the process of rejuvenating and healing of wounds.

2. Description of the Prior Art

It is known that during substance losses from wounds, operations or degenerative diseases, burns or bed-sores, the healing process proceeds in two different ways:
a) First, healing by placing together and suturing the edges of the wound, to protect the deep layers of the wound.
b) Second, healing by connective granulation of from the deep layers to make up the substance loss and thereafter healing the superficial layers of the wound. This latter process is necessarily much longer than the former.

In order to accelerate these processes, many types of substances are used to protect the wound and to avoid or fight contamination. These are most often creams or substances containing antiseptics, antibiotics, vitamin A and plants. Despite these precautions and these treatments the healing processes sometimes fail for many intrinsic or extrinsic reasons.

However, whatever the healing type or the treatments used are, complete tissue rejuvenation requires between 45 to 60 days.

SUMMARY OF THE INVENTION

The product according to the invention is obtained, on the one hand, directly from a ground material made up of the freeze-dried cells of the mollusc mantle and, on the other hand, from the ground material of the pearl testa of the mollusc from which either the organic fraction or the mineral fraction is used or both.

DETAILED DESCRIPTION OF THE PREFERRED EMBODIMENTS

The product according to the invention, in a first preferential way, is obtained in the following manner: after crushing and grinding the pearl testa of the mollusc, the residue obtained is washed and cleaned in an ultrasound jar, and and is then subjected to an enzymatic liquid treatment either with carbonic anhydrase or trypsin or any other enzyme, followed by an acid treatment to deactivate the enzyme.

The residue is washed with demineralized water, subjected to an evaporation treatment at 50° C. over 48 hours, then thinned out with demineralized water and centrifuged. According to a second method of fabrication, a dilacerate of the mollusc mantle is submitted to a thermal treatment in a vacuum for 4 hours. The obtained jelly is filtered on a diaphragm, concentrated by centrifugation and freeze-dried.

The product according to the invention can be obtained by mixing the two phases in order to obtain a gel, a cream or a solution.

The product according to the invention is mixed with vehicles having chemical properties which enhance its effects and promote penetration into the wound. These vehicles can be as follows without being limited by this list: menthol, camphor, benzoin, citric acid, methyl oxibenzoate, cetyl alcohol, stearyl alcohol, officinal vaseline, glycerine, purified water, vitamin A, algae extract, calcium hydroxide and copra extract.

The product according to the invention is intended to appreciably accelerate the healing by stimulation of the cytoplasmic activity of the fibroblasts, thereby inducing their proliferation in a few hours, and this is due to the invention's eutrophic and healing properties.

Some in vivo experiments have shown that the product according to the invention brings about an acceleration and an increase in volume of the healing bud as well as a very rapid coaptation of the wound edges.

The following examples show applications of the product according to the invention.

Two losses of cutaneous substances having 10 mm diameter involving the epiderm and the derm are effected on an animal. One is coated of the sterilized product according to the invention, the other is covered with an occlusive dressing. The formation of a healing bud is observed 48 hours later, with cellular proliferation and decrease of two thirds of the bleeding surface. Complete healing occurs after 6 days, whereas the control wound covered with an occlusive dressing heals after 17 days.

The product according to the invention is sterilized and applied on a perforated plantar sore in evolution for 15 years. It is known that the perforated plantar sore is an ailment of the skin and the muscles with frequent occurrence in diabetics, characterized by a perforation of the plantar arch of the foot at the support points, the heel and the metatarsus. This loss of substance occurs as a lesion of variable diameter and depth, the edges of which are atonic because the vascularization has completely disappeared, which lesion is sometimes infected, never evolves towards spontaneous healing and is insensitive to any treatment. In the above-mentioned example, one can see after a week a spectacular decrease of the diameter and depth of the lesion as well as a net revascularization of its edges. The healing bud fills up the lesion after 15 days, the complete recovery is obtained in 3 weeks by rejuvenation of the corneal stratum.

A third example concerns the use of the product according to the invention in a cosmetic application: after rubefaction of the right and left jugal areas, only one area is coated with the product according to the invention, the other one acting as control. Just after the application of the product according to the invention, a sedation of the pain due to burns is noted, 48 hours afterwards, a partial rejuvenation of the superficial layer of the epiderm occurs with complete disparition of the hyperhemia and 6 days later the smooth and normal aspect of the epiderm shows the evidence of a complete tissue rejuvenation of the superficial layer.

A fourth example concerns the utilization of the product according to the invention on a second degree burn: the product according to the invention is applied as a cream on the whole surface of the burnt area. As soon as the product according to the invention is applied, the sensation of burning disappears totally and a considerable diminution of the bleeding surface is clinically noted after 48 hours as well as the beginning of new pigmentation of the epiderm.

All these experiments revealed the stimulative action of the regulated process of cellular proliferation due to the product according to the invention as well as its eutrophic, antalgic, healing and antiphlogistic properties.

One of ordinary skills in the art can prepare a gel, a cream, a solution each time he wants to obtain an eutrophic, regenerating, antalgic, healing and antiphlogistic action, having as a constituent either the organomineral complex of the pearl testa of bivalved molluscs such as *Pinctada maxima* and others, or a freeze-dried product of the cells of the mantle originating from the organic or mineral fraction either of which may be used in association with one or several above noted vehicles or substances.

We claim:

1. A cutaneous healing composition comprising an effective amount of a product obtained by the process comprising:

a) subjecting cells from the mantle of the bivalved mollusc *Pinctada maxima* to a thermal treatment in a vacuum;

b) freeze-drying said thermally-treated cells;

c) mechanically grinding the pearl testa of the bivalved mollusc *Pinctada maxima*;

d) subjecting the mechanically ground pearl testa to an ultrasound treatment and then to an enzymatic treatment; and e) mixing the material obtained in step b) with the material obtained in step d).

2. The composition of claim 1 wherein the material obtained in step d) is subjected to a chemical acid treatment for enzyme deactivation prior to step e).

3. The composition of claim 1 wherein the material obtained in step d) is subjected to an evaporation treatment at 50° C. prior to step e).

4. The composition of claim 1 wherein the material obtained in step a) is filtered on a diaphragm and concentrated by centrifugation prior to step b).

5. The composition of claim 1 wherein the product is in the form of a gel, cream or solution.

6. A composition comprising the product of claim 1 blended with a vehicle selected from the group consisting of menthol, camphor, benzoin, citric acid, methyl oxibenzoate, stearyl alcohol, officinal vaseline, glycerine, purified water, vitamin A, algae extract, calcium hydroxide and copra extract.

7. A dermatological composition comprising an effective amount of the product of claim 1.

8. A cosmetic composition comprising an effective amount of the product of claim 1.

9. The composition of claim 1 wherein carbonic anhydrase or trypsin is used in the enzymatic treatment of step d).

10. A composition comprising the product of claim 1 blended with a vehicle that accentuates the healing effects of the product and promotes the penetration of the product into the skin.

11. A method of preparing a cutaneous healing composition comprising the steps of:

a) subjecting cells from the mantle of the bivalved mollusc *Pinctada maxima* to a thermal treatment in a vacuum;

a) freeze-drying said thermally-treated cells;

c) mechanically grinding the pearl testa of the bivalved mollusc *Pinctada maxima*;

d) subjecting the mechanically ground pearl testa to an ultrasound treatment and then to an enzymatic treatment; and e) mixing the material obtained in step b) with the material obtained in step d).

12. The method of claim 11 further comprising the step of subjecting the material obtained in step d) to a chemical acid treatment for enzyme deactivation prior to step e).

13. The method of claim 11 further comprising subjecting the material obtained in step d) to an evaporation treatment at 50° C. prior to step e).

14. The method of claim 11 further comprising subjecting the material obtained in step a) to filtration on a diaphragm and concentration by centrifugation prior to step e).

15. The method of claim 11 further comprising the step of formulating the composition in the form of a gel, cream or solution.

16. The method of claim 11 wherein carbonic anhydrase or trypsin is used in the enzymatic treatment of step d).

* * * * *